(12) United States Patent
Choi et al.

(10) Patent No.: US 9,944,741 B2
(45) Date of Patent: Apr. 17, 2018

(54) MODIFIED CONJUGATED DIENE POLYMER, METHOD FOR PREPARING SAME, AND RUBBER COMPOSITION CONTAINING SAME

(71) Applicant: LG Chem, Ltd., Seoul (KR)

(72) Inventors: Heungyeal Choi, Daejeon (KR); Noma Kim, Daejeon (KR); Yujin Kim, Daejeon (KR); Heseung Lee, Daejeon (KR); Kiseok Son, Daejeon (KR)

(73) Assignee: LG Chem, Ltd. (KR)

( * ) Notice: Subject to any disclaimer, the term of this patent is extended or adjusted under 35 U.S.C. 154(b) by 161 days.

(21) Appl. No.: 14/909,902

(22) PCT Filed: Nov. 14, 2014

(86) PCT No.: PCT/KR2014/010962
§ 371 (c)(1),
(2) Date: Feb. 3, 2016

(87) PCT Pub. No.: WO2015/072781
PCT Pub. Date: May 21, 2015

(65) Prior Publication Data
US 2016/0159957 A1 Jun. 9, 2016

(30) Foreign Application Priority Data

Nov. 15, 2013 (KR) .................. 10-2013-0138840
Nov. 14, 2014 (KR) .................. 10-2014-0158674

(51) Int. Cl.
| | | |
|---|---|---|
| *C08F 236/14* | (2006.01) | |
| *C08K 3/36* | (2006.01) | |
| *C08K 3/04* | (2006.01) | |
| *C07F 7/18* | (2006.01) | |
| *C08C 19/44* | (2006.01) | |
| *B60C 1/00* | (2006.01) | |
| *C08C 19/00* | (2006.01) | |
| *C08C 19/22* | (2006.01) | |
| *C08C 19/25* | (2006.01) | |
| *C08C 19/26* | (2006.01) | |
| *C08F 236/10* | (2006.01) | |
| *C08L 9/00* | (2006.01) | |
| *C08L 15/00* | (2006.01) | |

(52) U.S. Cl.
CPC .......... *C08F 236/14* (2013.01); *B60C 1/0016* (2013.01); *C07F 7/1836* (2013.01); *C07F 7/1844* (2013.01); *C08C 19/00* (2013.01); *C08C 19/22* (2013.01); *C08C 19/25* (2013.01); *C08C 19/26* (2013.01); *C08C 19/44* (2013.01); *C08F 236/10* (2013.01); *C08K 3/04* (2013.01); *C08K 3/36* (2013.01); *C08L 9/00* (2013.01); *C08L 15/00* (2013.01)

(58) Field of Classification Search
CPC .... C07F 7/1836; C07F 236/14; C07F 236/10; C07F 19/44; C07F 7/1844; C08L 15/00; C08L 9/00; C08C 19/44; C08C 19/00; C08C 19/22; C08C 19/25; C08C 19/26; C08F 236/14; C08F 236/10; C08F 3/0033; C08F 3/36; C08F 3/04; C08F 3/013; C08K 3/36; C08K 3/04; C08K 3/0033; B60C 1/0016; B32B 2/00
See application file for complete search history.

(56) References Cited

U.S. PATENT DOCUMENTS

| | | | | |
|---|---|---|---|---|
| 5,508,333 | A * | 4/1996 | Shimizu | C08C 19/44 524/423 |
| 2010/0099795 | A1 | 4/2010 | Uesaka | |
| 2013/0023624 | A1 | 1/2013 | Sekikawa et al. | |
| 2014/0114014 | A1 * | 4/2014 | Tokimune et al. | C08K 3/36 524/547 |
| 2014/0243476 | A1 | 8/2014 | Lee et al. | |
| 2014/0256847 | A1 | 9/2014 | Sato et al. | |
| 2014/0275430 | A1 | 9/2014 | Ishino et al. | |
| 2016/0096909 | A1 | 4/2016 | Sekikawa et al. | |

FOREIGN PATENT DOCUMENTS

| | | |
|---|---|---|
| CN | 101724185 A | 6/2010 |
| CN | 102791743 A | 11/2012 |
| EP | 2003146 A2 | 12/2008 |
| JP | 2005290355 A | 10/2005 |
| JP | 2006257260 A | 9/2006 |
| JP | 2012153764 A | 8/2012 |
| JP | 2013082840 A | 5/2013 |
| JP | 2013133387 A | 7/2013 |
| JP | 2013139491 A | 7/2013 |
| JP | 5394877 B2 | 1/2014 |

(Continued)

OTHER PUBLICATIONS

Extended Search Report from European Application No. 14862792.0, dated Oct. 14, 2016.

(Continued)

*Primary Examiner* — Nathan M Nutter

(57) ABSTRACT

Disclosed is a method of preparing a modified conjugated diene-based polymer, including (a) polymerizing a conjugated diene monomer, or a conjugated diene monomer and an aromatic vinyl monomer, using the compound represented by Chemical Formula 1 in the presence of a hydrocarbon solvent, thus forming an active polymer having an alkali metal end, and (b) coupling or reacting the active polymer with the compound represented by Chemical Formula 2.

17 Claims, No Drawings

(56) References Cited

FOREIGN PATENT DOCUMENTS

| KR | 20120130253 A | 11/2012 |
| WO | 2007114203 A1 | 10/2007 |
| WO | 2013018424 A1 | 2/2013 |
| WO | 2013077020 A1 | 5/2013 |
| WO | 2013077021 A1 | 5/2013 |
| WO | 2013119006 A1 | 8/2013 |

OTHER PUBLICATIONS

Search Report from Office Action from Chinese Application No. 201480045549.0, dated Oct. 14, 2016.
International Search Report for Application No. PCT/KR2014/010962 dated Feb. 13, 2015.

\* cited by examiner

MODIFIED CONJUGATED DIENE POLYMER, METHOD FOR PREPARING SAME, AND RUBBER COMPOSITION CONTAINING SAME

CROSS REFERENCES TO RELATED APPLICATION

The present application is a national phase entry under 35 U.S.C. § 371 of International Application No. PCT/KR2014/010962, filed Nov. 14, 2014, which claims priority from Korean Patent Application No. KR 10-2013-0138840, filed Nov. 15, 2013 and Korean Patent Application No. KR 10-2014-0158674, filed Nov. 14, 2014, all of which are incorporated herein by reference.

TECHNICAL FIELD

The present invention relates to a method of preparing a modified conjugated diene-based polymer, and more particularly, to a method of preparing a modified conjugated diene-based polymer having superior heat build-up, tensile strength, wear resistance, and wet skid resistance, a modified conjugated diene-based polymer prepared thereby, and a rubber composition including the modified conjugated diene-based polymer.

BACKGROUND ART

With the recent trends in the vehicle industry, there is always the need for increased durability, stability and fuel economy, and continuous efforts to meet such needs have been made.

In particular, many attempts have been made to enhance the properties of rubber, which is the material for vehicle tires, especially tire treads, which are in contact with roads. The rubber composition for vehicle tires includes a conjugated diene-based polymer such as polybutadiene or a butadiene-styrene copolymer. To improve the performance of vehicle tires, research is currently ongoing into mixing a conjugated diene-based rubber composition with various enhancers.

The present inventors have proposed the present invention to develop, as a material for a tire tread, rubber having superior heat build-up, tensile strength, wear resistance, and wet skid resistance.

DISCLOSURE

Technical Problem

An object of the present invention is to provide a modified conjugated diene-based polymer having superior heat build-up, tensile strength, wear resistance, and wet skid resistance, and a method of preparing the same.

Another object of the present invention is to provide a modified conjugated diene-based polymer rubber composition including the modified conjugated diene-based polymer.

Still another object of the present invention is to provide a modifier for use in preparing the modified conjugated diene-based polymer.

Yet another object of the present invention is to provide a tire including the rubber composition.

Technical Solution

In order to accomplish the above objects, the present invention provides a method of preparing a modified conjugated diene-based polymer, comprising: (a) polymerizing a conjugated diene monomer, or a conjugated diene monomer and an aromatic vinyl monomer, using the compound represented by Chemical Formula 1 below in the presence of a hydrocarbon solvent, thus forming an active polymer having an alkali metal end; and (b) coupling or reacting the active polymer with the compound represented by Chemical Formula 2 below:

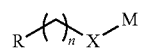

[Chemical Formula 1]

in Chemical Formula 1, R is a nitrogen-containing group, X is a hydrocarbon obtained by polymerizing a conjugated diene monomer or an aromatic vinyl monomer, n is an integer of 1 to 10, and M is an alkali metal; and

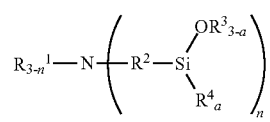

[Chemical Formula 2]

in Chemical Formula 2, $R^1$ is a C1-C8 alkyl group or alkylsilyl group, $R^2$ is a C1-C8 alkylene group, $R^3$ and $R^4$ are each independently a C1-C8 alkyl group, a is an integer of 0 to 2, and n is an integer of 1 to 3.

In addition, the present invention provides a modified conjugated diene-based polymer prepared by the above method, as represented by Chemical Formula 3 below:

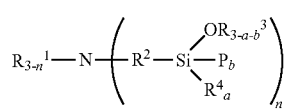

[Chemical Formula 3]

in Chemical Formula 3, $R^1$ is a C1-C8 alkyl group or alkylsilyl group, $R^2$ is a C1-C8 alkylene group, $R^3$ and $R^4$ are each independently a C1-C8 alkyl group, P is a conjugated diene-based polymer chain, a is 0, 1, or 2, b is 1, 2, or 3, a+b is 1, 2, or 3, and n is an integer of 1 to 3.

In addition, the present invention provides a modified conjugated diene-based polymer rubber composition, comprising a modified conjugated diene-based polymer prepared by the above method.

In addition, the present invention provides a modifier comprising the compound represented by Chemical Formula 2 below:

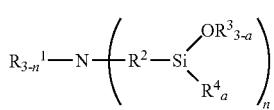

[Chemical Formula 2]

in Chemical Formula 2, $R^1$ is a C1-C8 alkyl group or alkylsilyl group, $R^2$ is a C1-C8 alkylene group, $R^3$ and $R^4$ are each independently a C1-C8 alkyl group, a is an integer of 0 to 2, and n is an integer of 1 to 3.

In addition, the present invention provides a tire or tire tread comprising the modified conjugated diene-based polymer rubber composition.

Advantageous Effects

According to the present invention, a modified conjugated diene-based polymer having superior heat build-up, tensile strength, wear resistance, and wet skid resistance can be prepared, and can be used for a rubber composition for a tire.

BEST MODE

Hereinafter, a detailed description will be given of the present invention.

The present invention addresses a method of preparing a modified conjugated diene-based polymer, comprising: (a) polymerizing a conjugated diene monomer, or a conjugated diene monomer and an aromatic vinyl monomer, using the compound represented by Chemical Formula 1 below, in the presence of a hydrocarbon solvent, thus forming an active polymer having an alkali metal end; and (b) coupling or reacting the active polymer with the compound represented by Chemical Formula 2 below.

[Chemical Formula 1]

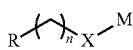

in Chemical Formula 1, R is a nitrogen-containing group, X is a hydrocarbon obtained by polymerizing a conjugated diene monomer or an aromatic vinyl monomer, n is an integer of 1 to 10, and M is an alkali metal; and

[Chemical Formula 2]

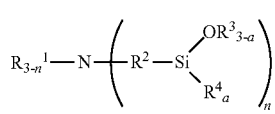

in Chemical Formula 2, $R^1$ is a C1-C8 alkyl group or alkylsilyl group, $R^2$ is a C1-C8 alkylene group, $R^3$ and $R^4$ are each independently a C1-C8 alkyl group, a is an integer of 0 to 2, and n is an integer of 1 to 3.

In the present invention, the conjugated diene monomer may include, but is not necessarily limited to, at least one selected from the group consisting of 1,3-butadiene, 2,3-dimethyl-1,3-butadiene, piperylene, 3-butyl-1,3-octadiene, isoprene, and 2-phenyl-1,3-butadiene.

In the present invention, the aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

The amount of the aromatic vinyl monomer is 0.0001 to 40 wt %, preferably 10 to 35 wt %, and more preferably 20 to 30 wt %, based on 100 wt % in total of the conjugated diene monomer and the aromatic vinyl monomer.

The hydrocarbon solvent may be exemplified by a hydrocarbon, or may include at least one selected from the group consisting of n-pentane, n-hexane, n-heptane, isooctane, cyclohexane, toluene, benzene, and xylene, but is not limited thereto.

In Chemical Formula 1, the nitrogen-containing group may include an amino group; an alkylamino group, such as methylamino, dimethylamino, ethylamino, propylamino, butylamino, and cyclohexylamino; and an arylamino group, such as phenylamino, tolylamino, and naphthylamino.

In Chemical Formula 1, n is an integer from 1 to 10. Given the above range, the resulting tire may exhibit superior heat build-up, tensile strength, wear resistance, and wet skid resistance.

In Chemical Formula 1, M is an alkali metal, which may be any one selected from the group consisting of lithium, sodium, potassium, rubidium, and cesium.

For example, the compound represented by Chemical Formula 1 may be a compound represented by Chemical Formula 4 below.

[Chemical Formula 4]

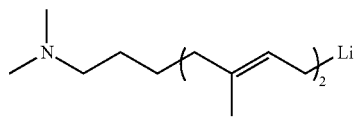

In an embodiment of the present invention, the compound represented by Chemical Formula 1 may be used in an amount of 0.01 to 10 mmol, 0.05 to 5 mmol, 0.1 to 2 mmol, or 0.1 to 1 mmol, based on 100 g in total of the monomer. When the amount of the compound represented by Chemical Formula 1 falls in the above range, a conjugated diene-based polymer optimal for use in preparing a modified conjugated diene-based polymer may be obtained.

The active polymer having the alkali metal end indicates a polymer comprising a polymer anion and an alkali metal cation, which are linked with each other.

In the method of preparing the modified conjugated diene-based polymer according to the present invention, the polymerizing in (a) may be performed with the additional use of a polar additive.

The polar additive may be a base, or may include ether, amine, or mixtures thereof, and may be specifically selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine. Preferably useful is ditetrahydropropylpropane, triethylamine or tetramethylethylenediamine.

The polar additive is used in an amount of 0.001 to 50 g, preferably 0.001 to 10 g, and more preferably 0.005 to 1 g, based on 100 g in total of the added monomer.

Also, the polar additive is used in an amount of 0.001 to 10 g, preferably 0.005 to 1 g, and more preferably 0.005 to 0.1 g, based on 1 mmol in total of the added compound represented by Chemical Formula 1.

When the conjugated diene monomer and the aromatic vinyl monomer are copolymerized, it is easy to prepare a block copolymer due to the difference in the reaction rates therebetween. However, when the polar additive is added, the low reaction rate of the aromatic vinyl monomer may be increased to thus induce the microstructure of the corresponding copolymer, for example, a random copolymer.

In (a), the polymerizing may be exemplified by anionic polymerization.

Also, the polymerizing in (a) may be living anionic polymerization for forming an active end through a growth reaction by anions.

Also, the polymerizing in (a) may be high-temperature polymerization or room-temperature polymerization.

High-temperature polymerization is a polymerization process including adding an organometallic compound and then applying heat to increase the reaction temperature, and room-temperature polymerization is a polymerization process that takes place in such a way that heat is not applied after the addition of an organometallic compound.

The polymerizing in (a) is carried out at a temperature ranging from −20 to 200° C., preferably 0 to 150° C., and more preferably 10 to 120° C.

In (b), the active polymer formed in (a) is coupled or reacted with the compound represented by Chemical Formula 2 below, thus preparing the modified conjugated diene-based polymer represented by Chemical Formula 3:

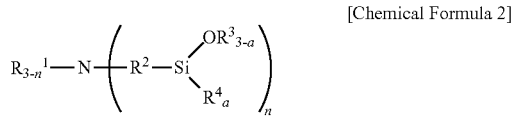

[Chemical Formula 2]

in Chemical Formula 2, $R^1$ is a C1-C8 alkyl group or alkylsilyl group, $R^2$ is a C1-C8 alkylene group, $R^3$ and $R^4$ are each independently a C1-C8 alkyl group, a is an integer of 0 to 2, and n is an integer of 1 to 3.

For example, the compound represented by Chemical Formula 2 may be a compound represented by Chemical Formula 5 below.

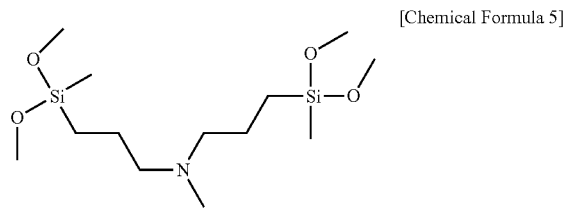 [SMILES: CO[Si](C)(CCCN(C)CCC[Si](C)(OC)OC)OC]

[Chemical Formula 5]

Also, (b) may be performed at 0 to 90° C. for 1 min to 5 hr.

According to the present invention, the method of preparing the modified conjugated diene-based polymer may be carried out in a batch manner, or alternatively in a continuous manner using at least one reactor.

The molar ratio of the compound represented by Chemical Formula 1 and the compound represented by Chemical Formula 2 is, for example, 1:0.1 to 1:10, and preferably 1:0.3 to 1:2. Given the above molar ratio, the conjugated diene-based polymer may undergo a modification reaction to ensure optimal performance.

According to the present invention, the method of preparing the modified conjugated diene-based polymer may be carried out in a batch manner, or alternatively in a continuous manner using at least one reactor.

In addition, the present invention addresses a modified conjugated diene-based polymer prepared by the above method, as represented by Chemical Formula 3 below:

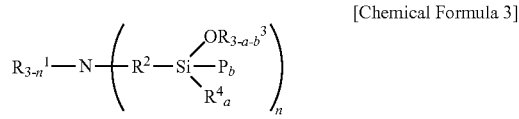

[Chemical Formula 3]

in Chemical Formula 3, $R^1$ is a C1-C8 alkyl group or alkylsilyl group, $R^2$ is a C1-C8 alkylene group, $R^3$ and $R^4$ are each independently a C1-C8 alkyl group, P is a conjugated diene-based polymer chain, a is 0, 1, or 2, b is 1, 2, or 3, a+b is 1, 2, or 3, and n is an integer of 1 to 3.

The conjugated diene-based polymer chain represented by P in Chemical Formula 3 may be derived from a homopolymer of a conjugated diene monomer, or a copolymer of a conjugated diene monomer and an aromatic vinyl monomer.

The conjugated diene-based polymer chain may be a polymer chain comprising 0.0001 to 40 wt %, preferably 10 to 35 wt %, and more preferably 20 to 30 wt % of the aromatic vinyl monomer, based on 100 wt % in total of the conjugated diene monomer and the aromatic vinyl monomer.

The polymer chain comprising the conjugated diene monomer and the aromatic vinyl monomer may be, for example, a random polymer chain.

The modified conjugated diene-based polymer has a number average molecular weight of 1,000 to 2,000,000 g/mol, preferably 10,000 to 1,000,000 g/mol, and more preferably 100,000 to 500,000 g/mol.

The modified conjugated diene-based polymer has a vinyl content of 18 wt % or more, preferably 25 wt % or more, and more preferably 30 to 70 wt %. When the vinyl content of the modified conjugated diene-based polymer falls in the above range, the glass transition temperature of the polymer may be elevated, and thus, when such a polymer is applied to tires, the properties required of tires, such as running resistance and braking force, may be satisfied, and fuel economy may be improved.

The vinyl content indicates the amount of a monomer having a vinyl group, or the amount of not 1,4- but 1,2-added conjugated diene monomer based on 100 wt % of the conjugated diene monomer.

The modified conjugated diene-based polymer has a Mooney viscosity of 40 or more, preferably 40 to 100, and more preferably 45 to 90. Given the above Mooney viscosity range, it is possible to prepare a modified conjugated diene-based polymer having excellent processability, compatibility, heat build-up, tensile strength, wear resistance, fuel economy, and wet skid resistance.

The modified conjugated diene-based polymer has a polydispersity index (PDI) of 0.5 to 10, preferably 0.5 to 5, and more preferably 1.0 to 2.0.

The modified conjugated diene-based polymer may exhibit viscoelastic properties. When measured at 10 Hz using DMA after mixing with silica, Tan δ at 0° C. may be in the range of 0.6 to 1, or 0.9 to 1. Given the above Tan δ range, skid resistance or wet resistance may be significantly improved.

Also, Tan δ at 60° C. may be in the range of 0.06 to 0.09, or 0.07 to 0.08. Given the above Tan δ range, rolling resistance or rotational resistance (RR) may be significantly improved.

In addition, the present invention addresses a modifier comprising the compound represented by Chemical Formula 2 below:

[Chemical Formula 2]

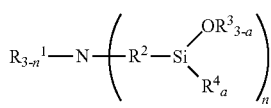

in Chemical Formula 2, $R^1$ is a C1-C8 alkyl group or alkylsilyl group, $R^2$ is a C1-C8 alkylene group, $R^3$ and $R^4$ are each independently a C1-C8 alkyl group, a is an integer of 0 to 2, and n is an integer of 1 to 3.

In addition, the present invention addresses a modified conjugated diene-based polymer rubber composition, comprising the modified conjugated diene-based polymer.

For example, the modified conjugated diene-based polymer rubber composition comprises 10 to 100 parts by weight of the modified conjugated diene-based polymer, and 0.1 to 200 parts by weight of an inorganic filler based on 100 parts by weight of the modified conjugated diene-based polymer.

The amount of the inorganic filler may be 10 to 150 parts by weight, or 50 to 100 parts by weight.

The inorganic filler may include, for example, carbon black, a silica-based filler, or mixtures thereof.

Alternatively, the inorganic filler may be silica. In this case, dispersibility is greatly improved and the end of the modified conjugated diene-based polymer of the invention is coupled (capped) with silica particles, thereby significantly decreasing hysteresis loss.

The modified conjugated diene-based polymer rubber composition may further comprise an additional conjugated diene-based polymer.

The additional conjugated diene-based polymer may include SBR (styrene-butadiene rubber), BR (butadiene rubber), natural rubber, or mixtures thereof.

SBR may be exemplified by SSBR (solution styrene-butadiene rubber).

The modified conjugated diene-based polymer rubber composition according to the present invention may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, in which the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

Also, the modified conjugated diene-based polymer rubber composition may further comprise 1 to 100 parts by weight of oil.

The oil may be exemplified by mineral oil or a softener.

The oil may be used in an amount of, for example, 10 to 100 parts by weight, or 20 to 80 parts by weight, based on 100 parts by weight of the conjugated diene-based polymer. When the amount of oil falls in the above range, desired properties may be exhibited, and the rubber composition may be appropriately softened, thus improving processability.

In addition, the present invention addresses a tire or tire tread comprising the rubber composition.

A better understanding of the present invention may be obtained via the following examples, which are set forth to illustrate but are not to be construed as limiting the present invention, and those skilled in the art will appreciate that diverse variations or substitutions are possible, without departing from the spirit of the present invention. Accordingly, such variations or substitutions fall within the scope of the present invention as defined in the accompanying claims.

Example 1: Preparation of Conjugated Diene-Based Polymer 270 g of styrene, 710 g of 1,3-butadiene, 5000 g of n-hexane, and 0.9 g of 2,2-bis(2-oxoranyl)propane as a polar additive were placed in a 20 L autoclave reactor, and then the temperature inside the reactor was elevated to 40° C. When the temperature inside the reactor reached 40° C., 4.3 mmol of 3-(dimethylamino)-1-propyllithium-(isoprene)$_2$ was placed in the reactor, followed by an adiabatic heating reaction. About 20 min after the adiabatic heating reaction, 20 g of 1,3-butadiene was added. After 5 min, 4.3 mmol of bis(triethoxysilylpropyl)-N-methylamine was added, and the reaction was carried out for 15 min. Thereafter, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 2: Preparation of Conjugated Diene-Based Polymer

Three reactors were prepared. Among them, the first and the second reactor were used as polymerization reactors, and the third reactor was used as a modification reactor.

Styrene, 1,3-butadiene, and n-hexane, without impurities such as water, were mixed at rates of 1.788 kg/h, 4.477 kg/h, and 4.176 kg/h, respectively, before being placed in the reactors. The resulting mixed solution was continuously fed into the first reactor. Subsequently, 2,2-bis(2-oxoranyl)propane, as a polar additive, and 3-(dimethylamino)-1-propyllithium-(isoprene)$_2$ were fed at rates of 3.6 g/h and 22.4 mmol/h, respectively, into the first reactor, and the temperature inside the reactor was adjusted to 70° C.

The polymer output from the first reactor was continuously fed into the upper portion of the second reactor, and a polymerization reaction was carried out while the temperature was maintained at 85° C. The polymer output from the second reactor was continuously fed into the upper portion of the third reactor, bis(triethoxysilylpropyl)-N-methylamine was continuously fed at a rate of 10.6 mmol/h, and a modification reaction was carried out. To the polymer output from the third reactor, a mixed solution of isopropylalcohol and an antioxidant (Wingstay-K) at a ratio of 8:2 was added at a rate of 32.5 g/h to stop the polymerization reaction, yielding a polymer.

100 parts by weight of the polymer thus obtained was mixed with 37.5 phr of TDAE oil (a distilled aromatic extract having a glass transition temperature of about −44 to about −50° C.), placed in water warmed with steam, stirred to remove the solvent, and then roll dried to remove the remaining solvent and water, yielding a modified conjugated diene-based polymer. The results of analysis of the modified conjugated diene-based polymer thus obtained are shown in Table 2 below.

Comparative Example 1: Preparation of Conjugated Diene-Based Polymer

A modified conjugated diene-based polymer was prepared in the same manner as in Example 1, with the exception that 4 mmol of n-butyllithium was used as the initiator. The results of analysis of the modified conjugated diene-based polymer thus obtained are shown in Table 1 below.

Comparative Example 2: Preparation of Conjugated Diene-Based Polymer

The results of analysis of a commercially available non-modified conjugated diene-based polymer (5025-2HM grade, made by LANXESS Deutschland GmbH) are shown in Table 1 below. For the non-modified conjugated diene-based polymer (TUFDENE™ 3835), RAE oil was used.

Comparative Example 3: Preparation of Conjugated Diene-Based Polymer

A modified conjugated diene-based polymer was prepared in the same manner as in Example 2, with the exception that n-butyllithium was added at 39.57 mmol/h as the initiator. The results of analysis of the modified conjugated diene-based polymer thus obtained are shown in Table 2 below.

Comparative Example 4: Preparation of Conjugated Diene-Based Polymer

The results of analysis of a commercially available non-modified conjugated diene-based polymer (5025-2HM grade, made by LANXESS Deutschland GmbH) are shown in Table 2 below.

For the non-modified conjugated diene-based polymer (TUFDENE™ 3835), RAE oil was used, in lieu of TDAE oil.

The conjugated diene-based polymers prepared in Examples 1 and 2 and Comparative Examples 1 to 4 were analyzed through the following methods.

a) Mooney viscosity: Two samples having a weight of 15 g or more were preheated for 1 min and then measured at 100° C. for 4 min using an MV-2000, made by ALPHA Technologies.

b) Styrene monomer (SM) and Vinyl content: Measurement was conducted using NMR.

c) Weight average molecular weight (Mw), Number average molecular weight (Mn), and Polydispersity Index (PDI): Measurement was conducted via GPC at 40° C. For this, a column was composed of a combination of two PLgel Olexis columns and one PLgel mixed-C column, made by Polymer Laboratories, and all newly replaced columns were mixed bed type columns. Also, polystyrene (PS) was a GPC standard material for the calculation of molecular weight.

TABLE 1

|  |  | Ex. 1 | C. Ex. 1 | C. Ex. 2 |
|---|---|---|---|---|
| Sample |  | A | B | C |
| Initiator (mmol) | n-Butyllithium | — | 4 | — |
|  | a* | 4.3 | — | — |
| Polar additive (g) |  | 0.9 | 0.9 | — |
| Modifier (mmol) | b* | 4.3 | — | — |
| Mooney viscosity (MV) |  | 61 | 50 | 61 |
| TDAE oil (phr) |  | — | — | RAE 37.5 |
| NMR (%) | SM | 27 | 27 | 25 |
|  | Vinyl | 43 | 43 | 49 |
| GPC (×10⁴) | Mn | 34 | 30 | 39 |
|  | Mw | 46 | 40 | 69 |
|  | PDI | 1.4 | 1.3 | 1.8 | a*: 3-(Dimethylamino)-1-propyllithium-(isoprene)₂
b*: Bis(triethoxysilylpropyl)-N-methylamine
C: 5025-2HM grade, made by LANXESS Deutschland GmbH

TABLE 2

|  |  | Ex. 2 | C. Ex. 3 | C. Ex. 4 |
|---|---|---|---|---|
| Sample |  | D | E | F |
| Initiator (mmol) | n-Butyllithium | — | 39.57 | — |
|  | a* | 22.4 | — | — |
| Polar additive (g/h) |  | 3.6 | 3.6 | — |
| Modifier (mmol) | b* | 10.6 | 10.6 | — |
| Mooney viscosity (MV) |  | 89 | 70 | — |
| TDAE oil (phr) |  | 37.5 | 37.5 | RAE 37.5 |
| NMR (%) | SM | 36 | 36 | 36 |
|  | Vinyl | 26 | 26 | 26 |
| GPC (×10⁴) | Mn | 48 | 47 | 33 |
|  | Mw | 107 | 93 | 94 |
|  | PDI | 2.2 | 2.0 | 2.8 | a*: 3-(Dimethylamino)-1-propyllithium-(isoprene)₂
b*: Bis(triethoxysilylpropyl)-N-methylamine
F: 5025-2HM grade, made by LANXESS Deutschland GmbH Preparation of Conjugated Diene-Based Polymer Rubber Composition The conjugated diene-based polymer rubber compositions of Preparation Examples 1 and 2 and Comparative Preparation Examples 1 to 4 were prepared using, as raw rubber, samples A, B, C, D, E, and F, shown in Tables 1 and 2, under the mixing conditions set forth in Table 3 below. The unit of material in Table 2 is phr, based on 100 parts by weight of rubber.

Specifically, the conjugated diene-based polymer rubber composition was kneaded through primary kneading and secondary kneading. Upon primary kneading, raw rubber (conjugated diene-based polymer), a filler, an organosilane coupling agent, oil, zinc oxide, a stearic acid antioxidant, an anti-aging agent, wax and an accelerator were kneaded using a Banbury mixer provided with a temperature controller. For this, the temperature of the kneader was controlled, and a first mixture was obtained at a discharge temperature of 145 to 155° C. Upon secondary kneading, the first mixture was cooled to room temperature, after which rubber, sulfur and a vulcanization accelerator were placed in the kneader, followed by mixing at 100° C. or less, thus obtaining a second mixture. Finally, curing was performed at 100° C. for 20 min, yielding the conjugated diene-based polymer rubber compositions of Preparation Examples 1 and 2 using, as raw rubber, the polymers of Examples 1 and 2, and of Comparative Preparation Examples 1 to 4 using the polymers of Comparative Examples 1 to 4 as raw rubber.

TABLE 3

|  | Material | Amount (unit: phr) |
|---|---|---|
| Primary kneading | Rubber | 137.5 |
|  | Silica | 70.0 |
|  | Coupling agent | 11.2 |
|  | Oil | — |
|  | Zinc oxide | 3.0 |
|  | Stearic acid | 2.0 |
|  | Antioxidant | 2.0 |
|  | Anti-aging agent | 2.0 |
|  | Wax | 1.0 |
| Secondary kneading | Rubber accelerator | 1.75 |
|  | Sulfur | 1.5 |
|  | Vulcanization accelerator | 2.0 |
|  | Total weight | 234.0 |

The properties of the prepared rubber compositions were measured through the following methods.

1) Tensile Testing

According to a tensile testing method of ASTM 412, the tensile strength upon cutting a test sample and tensile stress (300% modulus) at 300% elongation were measured. To this end, a Universal Test Machine 4204, made by Instron, was used, and the tensile strength, modulus, and elongation were measured at a tensile speed of 50 cm/min at room temperature.

2) Viscoelasticity

A dynamic mechanical analyzer made by TA was used. When undergoing deformation under conditions of a frequency of 10 Hz in a distortion mode and a measurement temperature (ranging from −60 to 60° C.), the Tan δ of each sample was measured. The Payne effect was represented by the difference between the minimum and the maximum in the deformation range of 0.28 to 40%. The lower the Payne effect, the higher the dispersibility of the filler such as silica. When Tan δ at 0° C. that is a low temperature was increased, wet skid resistance became superior, and when Tan δ at 60° C. that is a high temperature was decreased, hysteresis loss was reduced, and low rolling resistance of tires, namely, improved fuel economy, resulted. Tables 4 and 5 below show the properties of the vulcanized rubber.

TABLE 4

|  | Prep. Ex. 1 | C. Prep. Ex. 1 | C. Prep. Ex. 2 |
|---|---|---|---|
| Sample | A | B | C |
| 300% Modulus (Kgf/cm$^2$) | 131 | 101 | 97 |
| Tensile strength (Kgf/cm$^2$) | 210 | 165 | 159 |
| Tanδ at 0° C. | 0.957 | 0.544 | 0.645 |
| Tanδ at 60° C. | 0.109 | 0.116 | 0.135 |
| ΔG' at 60° C. (Payne Effect) | 0.39 | 0.75 | 0.56 |

TABLE 5

|  | Prep. Ex. 2 | C. Prep. Ex. 3 | C. Prep. Ex. 4 |
|---|---|---|---|
| Sample | D | E | F |
| 300% Modulus (Kgf/cm$^2$) | 127 | 122 | 105 |
| Tensile strength (Kgf/cm$^2$) | 195 | 193 | 177 |
| Tanδ at 0° C. | 0.945 | 0.905 | 0.766 |
| Tanδ at 60° C. | 0.098 | 0.105 | 0.142 |
| ΔG' at 60° C. (Payne Effect) | 0.32 | 0.34 | 0.45 |

As is apparent from the results of Tables 4 and 5, the modified conjugated diene-based polymer rubber compositions of Preparation Examples 1 and 2 according to the present invention were significantly improved in 300% modulus (tensile stress) and tensile strength, compared to Comparative Preparation Examples 2 and 4, and also exhibited low Tan δ at 60° C. Thus, when manufacturing a tire using the modified conjugated diene-based polymer rubber composition of the invention, rolling resistance was decreased, whereby desired fuel efficiency resulted.

Also, the modified conjugated diene-based polymer rubber compositions of Preparation Examples 1 and 2 according to the present invention exhibited high Tan δ at 0° C., compared to Comparative Preparation Examples 1 to 4. Thus, when a tire was manufactured using the modified conjugated diene-based polymer rubber composition of the invention, high wet skid resistance resulted.

Also, the modified conjugated diene-based polymer rubber compositions of Preparation Examples 1 and 2 according to the present invention exhibited low ΔG' at 60° C., compared to Comparative Preparation Examples 1 to 4, thus improving wet skid resistance, rolling resistance, and silica dispersibility.

The invention claimed is:

1. A method of preparing a modified conjugated diene-based polymer, comprising:

(a) polymerizing a conjugated diene monomer or a conjugated diene monomer and an aromatic vinyl monomer with a compound represented by Chemical Formula 1 below using a hydrocarbon solvent, thus forming an active polymer having an alkali metal end; and (b) coupling or reacting the active polymer with a compound represented by Chemical Formula 2 below:

[Chemical Formula 1]

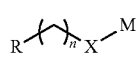

in Chemical Formula 1, R is an amino group, an alkylamino group or an arylamino group, X is a hydrocarbon obtained by polymerizing a conjugated diene monomer selected from the group consisting of 1,3-butadiene, 2,3-dimethyl-1,3-butadiene, piperylene, 3-butyl-1,3-octadiene, isoprene, and 2-phenyl-1,3-butadiene or an aromatic vinyl monomer selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene, n is an integer of 1 to 10, and M is an alkali metal; and

[Chemical Formula 2]

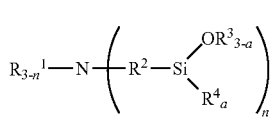

in Chemical Formula 2, $R^1$ is a C1-C8 alkyl group or alkylsilyl group, $R^2$ is a C1-C8 alkylene group, $R^3$ and $R^4$ are each independently a C1-C8 alkyl group, a is an integer of 0 to 2, and n is an integer of 1 to 3.

2. The method of claim 1, wherein the compound represented by Chemical Formula 1 is a compound represented by Chemical Formula 4 below.

[Chemical Formula 4]

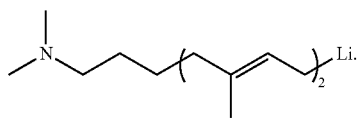

3. The method of claim 1, wherein the compound represented by Chemical Formula 1 is used in an amount of 0.01 to 10 mmol based on 100 g in total of the monomer.

4. The method of claim 1, wherein the compound represented by Chemical Formula 2 is a compound represented by Chemical Formula 5 below.

[Chemical Formula 5]

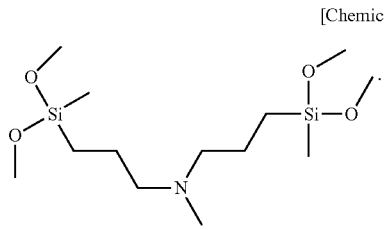

5. The method of claim 1, wherein a molar ratio of the compound represented by Chemical Formula 1 and the compound represented by Chemical Formula 2 is 1:0.1 to 1:10.

6. The method of claim 1, wherein the polymerizing in (a) is performed with additional use of a polar additive.

7. The method of claim 1, wherein the polar additive is added in an amount of 0.001 to 10 g based on 1 mmol in total of the compound represented by Chemical Formula 1.

8. A modified conjugated diene-based polymer, prepared by the method of claim 1, and represented by Chemical Formula 3 below:

[Chemical Formula 3]

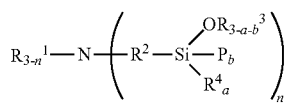

in Chemical Formula 3, $R^1$ is a C1-C8 alkyl group or alkylsilyl group, $R^2$ is a C1-C8 alkylene group, $R^3$ and $R^4$ are each independently a C1-C8 alkyl group, P is a conjugated diene-based polymer chain, a is 0, 1, or 2, b is 1, 2, or 3, a+b is 1, 2, or 3, and n is an integer of 1 to 3.

9. The modified conjugated diene-based polymer of claim 8, wherein the modified conjugated diene-based polymer has a number average molecular weight (Mn) of 1,000 to 2,000,000 g/mol.

10. The modified conjugated diene-based polymer of claim 8, wherein the modified conjugated diene-based polymer has a vinyl content of 10 wt % or more.

11. The modified conjugated diene-based polymer of claim 8, wherein the conjugated diene-based polymer chain is derived from a homopolymer of a conjugated diene monomer or a copolymer of a conjugated diene monomer and an aromatic vinyl monomer.

12. The modified conjugated diene-based polymer of claim 8, wherein the modified conjugated diene-based polymer includes 0.0001 to 50 wt % of an aromatic vinyl monomer based on 100 wt % in total of a conjugated diene monomer and the aromatic vinyl monomer.

13. The modified conjugated diene-based polymer of claim 8, wherein the modified conjugated diene-based polymer has a Mooney viscosity of 40 or more.

14. The modified conjugated diene-based polymer of claim 8, wherein the modified conjugated diene-based polymer has a polydispersity index (Mw/Mn) of 0.5 to 10.

15. A modified conjugated diene-based polymer rubber composition, comprising 10 to 100 parts by weight of the modified conjugated diene-based polymer of claim 8, and 0.1 to 200 parts by weight of an inorganic filler based on 100 parts by weight of the modified conjugated diene-based polymer.

16. The modified conjugated diene-based polymer rubber composition of claim 15, wherein the inorganic filler comprises at least one selected from the group consisting of a silica-based filler, carbon black, and mixtures thereof.

17. A tire or tire tread, comprising the modified conjugated diene-based polymer rubber composition of claim 15.

* * * * *